US00PP28667P3

(12) United States Plant Patent
Cain

(10) Patent No.: US PP28,667 P3
(45) Date of Patent: Nov. 21, 2017

(54) GRAPEVINE NAMED 'IFG TWENTY-THREE'

(50) Latin Name: ***Vitis interspecific* hybrid**
Varietal Denomination: IFG Twenty-three

(71) Applicant: David Cain, Bakersfield, CA (US)

(72) Inventor: David Cain, Bakersfield, CA (US)

(73) Assignee: INTERNATIONAL FRUIT GENETICS, LLC, Bakersfield, CA (US)

( * ) Notice: Subject to any disclaimer, the term of this patent is extended or adjusted under 35 U.S.C. 154(b) by 11 days.

(21) Appl. No.: 14/998,924

(22) Filed: Mar. 7, 2016

(65) Prior Publication Data

US 2017/0257993 P1 Sep. 7, 2017

(51) Int. Cl.
*A01H 5/08* (2006.01)

(52) U.S. Cl.
USPC ..... Plt./206

(58) Field of Classification Search
USPC ..... Plt./205, 206
See application file for complete search history.

*Primary Examiner* — Susan McCormick Ewoldt

(57) ABSTRACT

This invention is a new and distinct grapevine variety denominated 'IFG Twenty-three'. The new grapevine is characterized by producing naturally large seedless reddish black berries having a spherical shape with a mild fruity labrusca flavor somewhat similar to the Kyoho variety but smaller in size and seedless.

1 Drawing Sheet

Latin name of the genus and species claimed: *Vitis* interspecific hybrid.

Variety denomination: 'IFG Twenty-three'.

BACKGROUND OF THE INVENTION

The new and distinct grapevine described and claimed herein originated from a hand pollinated cross of the 01032-067-202, an unnamed seedling selection from the IFG breeding program, and the Arkansas 2798 (non-patented, non-released interspecific selection) hybridized in May 2006. The abortive seed traces were subsequently embryo cultured and the resulting population of plants was planted in the field in April 2007. The present variety of grapevine was selected as a single plant in October 2008 and was first asexually propagated by hardwood cuttings in December 2008 near Delano, Kern County, Calif. The resulting propagules were planted during April 2009 near Delano, Kern County, Calif. and were found to reproduce true-to-type through at least two generations of asexual reproduction.

BRIEF SUMMARY OF THE INVENTION

The new grapevine 'IFG Twenty-three' is characterized by producing naturally large seedless reddish black berries having a spherical shape with a mild fruity labrusca flavor somewhat similar to the Kyoho variety but smaller in size and seedless. Fruits normally ripen mid to late season about early to mid-September near Delano Calif. Fruits are fairly low in acidity, with medium dense firm texture, having occasionally noticeable seed traces and may be difficult to color in hot climatic conditions. Berries may occasionally split at the stylar end. Attachment of the berry to the pedicel is strong. Vines are productive and can be pruned to short spurs. The new grapevine differs from its maternal parent the 01032-067-202 by having dark red rather than light green berries and by having a medium strong fruity labrusca type flavor as opposed to the neutral flavor of the 01032-067-202. 'IFG Twenty-three' can be distinguished from its pollen parent, Arkansas 2798, by its dark reddish black color as opposed to full black color, by having round berries as opposed to obovoid berries and by having a mild labrusca flavor rather than a strong labrusca flavor of the Arkansas 2798.

The interspecific nature of the vine is very evident. Vines are very vigorous with a more horizontal growth habit and large leaves as compared to typical varieties of the *Vitis vinifera* species.

Grape breeders have used several native American grape species to improve hardiness, disease and insect resistance as well as incorporate aromatic flavors into the *vinifera* species. Previously introduced interspecific varieties have had very limited commercial success due to small fruit size, large seed traces, slipskin texture or lack of firmness. The new grapevine variety 'IFG Twenty-three' is being introduced because of its unique combination of labrusca flavor combined with firm texture, seedlessness, good adhesion of skin and flesh and naturally large berry size and its resemblance to the Kyoho grape.

BRIEF DESCRIPTION OF THE DRAWING

The accompanying photographic drawing in FIG. 1 illustrates in full color 'IFG Twenty-three'. The photograph was taken outdoors with indirect lighting. The colors are as nearly true as is reasonably possible in a color representation of this type. Mature leaves can be seen on the left side of the drawing. A mature fruit cluster is represented in the center of the drawing. A young shoot tip with tendrils and young leaves can be seen on the right side of the drawing along with a typical berry and a berry in cross-section.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published in 2001 by The Royal Horticultural Society, London, England.

Throughout this specification subjective description values conform to those set forth by the International Plant Genetic Resources Institute publication 'Descriptors for Grape' (*vitis* spp.) (1983) which was developed in collaboration with the Office International de la Vigne et du Vin (OIV) and the International Union for the Protection of New Varieties of Plants (UPOV).

The descriptive matter which follows pertains to 'IFG Twenty-three' plants grown in the vicinity of Delano, Kern County, Calif. during 2014, and is believed to apply to plants of the variety grown under similar conditions of soil and climate elsewhere:

VINE

General:
- *Vigor*.—Vigorous.
- *Density of foliage*.—Dense.
- *Productivity*.—Productive, producing 17.5 to 26.2 kg of fruit per vine.
- *Root stock*.—Own root.
- *Training method*.—Typically spur pruned leaving 2 bud spurs.

Trunk:
- *Trunk diameter of* 4-*year-old vines at* 30 *cm above the soil line*.—About 5.8 cm.
- *Shape*.—Somewhat stocky.
- *Straps*.—Very long and continuous.
- *Surface texture*.—Medium rough.
- *Inner bark color*.—The following colors were observed: Greyed-orange: 165A and 200B and 200C.

SHOOTS

Young shoot:
- *Form of tip*.—Wide open.
- *Distribution of anthocyanin coloration of tip*.—Piping (striped).
- *Intensity of anthocyanin coloration of tip*.—Weak.
- *Density of prostrate hairs of tip*.—Dense.
- *Density of erect hairs of tip*.—Absent.
- *Color*.—Yellow-green: 144A.

Woody shoot (mature canes):
- *Internode length*.—Medium, about 15.0 cm.
- *Width at node*.—About 1.7 cm.
- *Cross section*.—Elliptic to narrow elliptic.
- *Surface*.—Striate.
- *Main color*.—The following colors were observed: Greyed-orange: 166A and 166B and 166C and 166D.
- *Density of erect hairs on nodes*.—Medium.
- *Density of erect hairs on internodes*.—Sparse to medium.
- *Axillary shoot length at full bloom*.—Long, approximately 24.9 cm.

Flowering shoot:
- *Vigor during flowering*.—Very strong.
- *Attitude during flowering on shoots not tied*.—Drooping.
- *Color*.—Dorsal side of internodes — Yellow-green: 146C, with Red-purple stripes: 59B.
- *Color*.—Ventral side of internodes — Yellow-green: 146C.
- *Color*.—Dorsal side of nodes — Yellow-green: 146C, with Red-purple stripes: 59B.
- *Color*.—Ventral side of nodes — Yellow-green: 146C.
- *Density of prostrate hairs on nodes*.—Sparse.
- *Density of erect hairs on nodes*.—Sparse.
- *Density of prostrate hairs on internode*.—Sparse.
- *Density of erect hairs on internode*.—Very sparse.
- *Anthocyanin coloration of buds*.—Present.

Tendrils:
- *Distribution on the shoot* (*at full flowering*).—Discontinuous.
- *Length of tendril*.—Very long, about 39.7 cm.
- *Thickness of tendril* 2 *cm from base*.—About 3.2 mm.
- *Color*.—Yellow-green: N144A. Tendrils exposed to the sun can also have Red-purple stripes: 186A piped on the dorsal side of the tendrils.
- *Form*.—Bifurcated and trifurcated.
- *Number of consecutive tendrils*.—2.

LEAVES

Young leaves:
- *Color of upper surface of first four distal unfolded leaves*.—Yellow-green: 144A.
- *Average intensity of anthocyanin coloration of six distal leaves prior to flowering*.—Absent.
- *Density of prostrate hairs between veins* (*lower surface*).—Dense.
- *Density of prostrate hairs on veins* (*lower surface*).—Sparse.
- *Density of erect hairs between veins* (*lower surface*).—Sparse.
- *Density of erect hairs on veins* (*lower surface*).—Dense.

Mature leaves:
- *Average length*.—About 14.4 cm.
- *Average width*.—About 20.6 cm.
- *Mature leaf size*.—Large.
- *Shape of blade*.—Wedge-shaped.
- *Number of lobes*.—5.
- *Blade venation*.—Palmate.
- *Vein color*.—Yellow-green: 145C.
- *Anthocyanin coloration of main veins on upper side of blade*.—Absent to very weak.
- *Mature leaf profile*.—Undulate.
- *Blistering surface of blade upper surface*.—Weak to medium.
- *Leaf blade tip*.—In the plane of the leaf.
- *Undulation of margin*.—Medium.
- *Undulation of blade between main and lateral veins*.—Overall.
- *Shape of teeth*.—Mixture of both sides straight and both sides convex.
- *Length of teeth*.—Short.
- *Ratio length/width of teeth*.—Medium.
- *Shape of upper lateral sinuses*.—Lobes slightly overlapping.
- *Depth of upper lateral sinuses*.—Shallow.
- *General shape petiole sinus*.—Slightly open to closed.
- *Shape of base of upper leaf sinuses*.—V-shaped.
- *Tooth at petiole sinus*.—Occasionally present.
- *Density of prostrate hairs between veins on lower surface of blade*.—Sparse.
- *Density of erect hairs between veins on lower surface of blade*.—Sparse.

*Density of prostrate hairs on main veins on lower surface of blade*.—Sparse.
*Density of erect hairs on main veins on lower surface of blade*.—Dense.
*Density of prostrate hairs on main veins on upper surface of blade*.—Sparse.
*Density of erect hairs on main veins on upper surface of blade*.—Very sparse.
*Autumn coloration of leaves*.—Leaves can be a single color or a combination of colors, in a mottled pattern or on the edges of the leaves. The following colors were observed: Greyed-purple: 187A and 187B, and N186A and N186B and N186C and N186D, Greyed-orange: 34A and 34B, and Purple: N77A.

Upper surface:
*Color*.—Yellow-green: 146A.
*Anthocyanin coloration of main veins*.—Absent to very weak.
*Surface appearance*.—Semi-glossy.
*Blistering surface of blade*.—Weak to medium.

Lower surface:
*Color*.—Yellow-green: 147B.
*Anthocyanin coloration of main veins* (*lower surface*).—Weak.
*Glossiness*.—Weak.
*Surface texture*.—Rugose.
*Surface appearance*.—Dull.

Petiole:
*Length*.—About 11.2 cm.
*Diameter of petiole 2 cm from blade*.—About 4.0 mm.
*Petiole color*.—The following colors were observed: Yellow-green: 145B and 145C and Red-purple: 59A.
*Length of petiole compared to middle vein*.—Slightly shorter.
*Density of prostrate hairs on petiole*.—Sparse.
*Density of erect hairs on petiole*.—Dense.

Buds:
*Bud fruitfulness*.—Basal: mostly fruitful.
*Position of first fruitful shoot on previous season cane*.—1 $^{st}$ to 2$^{nd}$ node.
*Dormant bud length*.—About 8.1 mm.
*Dormant bud width in the proximal/distal plane*.—About 4 7 mm.
*Dormant bud color*.—Greyed-orange: 166A.
*Time of bud burst*.—Midseason; Mar. 8, 2014.

FLOWERS

General:
*Flower sex*.—Hermaphrodite.
*Length of first inflorescence*.—Long, about 18.4 cm long by 8.6 cm wide.
*Position of first flowering and fruiting node*.—3$^{rd\ node}$ (current season growth).
*Number of inflorescence per flowering shoot*.—2 to 3, about 2.1.
*Time of bloom*.—Early to medium as compared with similar varieties in the growing area of Delano, Calif.
*Date of full bloom*.—Apr. 25, 2014.

FRUIT

General:
*Ripening period*.—Late: approximately Sep. 16, 2014.
*Use*.—Fresh market.
*Keeping quality*.—Medium, remains commercially acceptable when stored up to 4 weeks at 0° C. and high relative humidity.
*Resistance to*.—Insects: Average typical of *Vitis vinifera* species. Diseases: Average typical of *Vitis vinifera* species.
*Refractometer test*.—Soluble solids: about 18.6 Brix.
*Brix/acid*.—About 56.4.
*Titratable acidity*.—About 0.33.
*Juice ph*.—About 4.02.

Cluster:
*Mature cluster length* (*peduncle excluded*).—About 26.6 cm.
*Mature cluster width*.—About 13.9 cm.
*Mature cluster weight*.—About 583 g.
*Bunch density*.—Medium loose.
*Number of berries*.—About 113.
*Form*.—Conical.

Peduncle:
*Lignification of peduncle*.—Weak.
*Length of peduncle*.—Long, approximately 7.9 cm.

Berry:
*Uniformity of size*.—Uniform.
*Single berry weight*.—About 6.3 g natural to about 7.3 g when treated with gibberellic acid.
*Shape*.—Round.
*Seeds*.—Contains small rudimentary seed traces, seed traces occasionally noticeable.
*Cross-section*.—Circular.
*Berry dimensions*.—Longitudinal axis: about 2.3 cm. Horizontal axis: about 2.1 cm.
*Berry firmness*.—Firm.
*Particular flavor*.—Labrusca.
*Bloom* (*cuticular wax*).—Medium heavy.
*Berry separation from pedicel*.—Medium strong.
*Flesh color*.—The following colors were observed: Greyed-white: 156B and 156C.
*Skin color* (*without bloom*).—The following colors were observed: Greyed-purple: N186A and N186B and N186C.

Skin:
*Thickness*.—Medium.
*Skin toughness*.—Medium to thin; not objectionable when chewing, may occasionally split at the stylar end.
*Reticulation*.—Absent.
*Tenacity*.—Tenacious to flesh.

What is claimed:

1. A new and distinct variety of grapevine as herein illustrated and described.

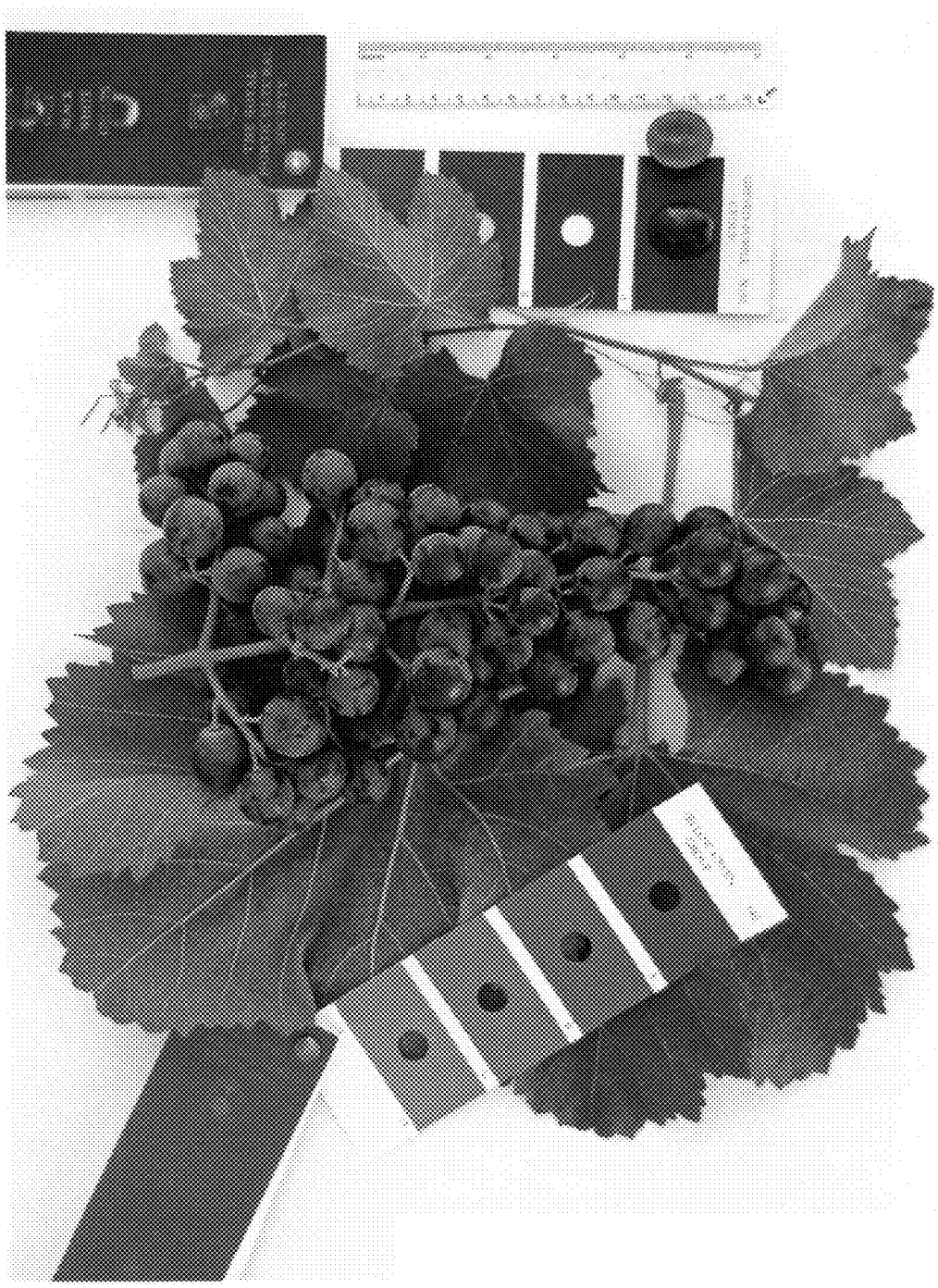

* * * * *